US008414597B2

(12) United States Patent
Kao et al.

(10) Patent No.: US 8,414,597 B2
(45) Date of Patent: Apr. 9, 2013

(54) APPARATUS FOR SUPPORTING AN ADJUSTABLE SURGICAL PLATFORM

(75) Inventors: Changquing C. Kao, Brentwood, TN (US); J. Michael Fitzpatrick, Nashville, TN (US); Robert F. Labadie, Nashville, TN (US); Peter E. Konrad, Old Hickory, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/161,383

(22) Filed: Jun. 15, 2011

(65) Prior Publication Data

US 2011/0295271 A1    Dec. 1, 2011

Related U.S. Application Data

(60) Continuation-in-part of application No. 12/849,241, filed on Aug. 3, 2010, now abandoned, which is a division of application No. 11/594,700, filed on Nov. 7, 2006, now Pat. No. 7,794, 469.

(60) Provisional application No. 60/734,052, filed on Nov. 7, 2005.

(51) Int. Cl.
*A61B 19/00*    (2006.01)

(52) U.S. Cl.
USPC ........................................................ 606/130

(58) Field of Classification Search .................. 600/415, 600/417, 424, 429; 606/108, 129, 130; 248/166, 248/170, 177, 181.1, 188.7, 514–516, 519, 248/523
See application file for complete search history.

(56) References Cited

U.S. PATENT DOCUMENTS

| 3,568,963 | A | * | 3/1971 | Koskinen ..................... 248/516 |
| 3,881,675 | A |   | 5/1975 | Matchett |
| 4,366,940 | A |   | 1/1983 | Vargas |
| 5,000,416 | A | * | 3/1991 | Fantasia ....................... 248/650 |
| 5,637,074 | A |   | 6/1997 | Andino et al. |
| 5,749,549 | A |   | 5/1998 | Ashjaee |
| 5,752,962 | A |   | 5/1998 | D'Urso |
| 5,810,712 | A |   | 9/1998 | Dunn |
| 5,903,995 | A |   | 5/1999 | Brubach |
| 6,471,711 | B2 |  | 10/2002 | Irie et al. |
| 6,579,281 | B2 |  | 6/2003 | Palmer et al. |
| 6,843,015 | B2 |  | 1/2005 | Sharp |
| 2002/0049451 | A1 | * | 4/2002 | Parmer et al. ................ 606/108 |
| 2002/0169460 | A1 |  | 11/2002 | Foster et al. |
| 2005/0070781 | A1 |  | 3/2005 | Dawant et al. |

* cited by examiner

*Primary Examiner* — Thomas McEvoy
(74) *Attorney, Agent, or Firm* — Tim Tingkang Xia, Esq.; Morris Manning & Martin, LLP

(57) ABSTRACT

In one aspect, an apparatus for supporting an adjustable surgical platform is disclosed. In one embodiment, the apparatus includes a supporting platform portion with a body portion that defines bore along a central axis. Arm portions with engaging means extend radially from the supporting platform portion. The apparatus also includes a shaft portion extending from the supporting platform portion in a first direction, with a shaft body portion that defines a bore along a longitudinal axis B. The bore of the shaft body portion is in communication with the bore of the supporting platform portion. The apparatus further includes a base portion connected to the shaft portion, and that defines a bore in communication with the bore of the shaft portion and the bore of the supporting platform portion. Mounting means are configured to secure the base portion to a region of interest of a living subject.

23 Claims, 9 Drawing Sheets

APPARATUS FOR SUPPORTING AN ADJUSTABLE SURGICAL PLATFORM

CROSS-REFERENCE TO RELATED PATENT APPLICATION

This application is a continuation-in-part of U.S. patent application Ser. No. 12/849,241, filed Aug. 3, 2010, entitled "ADJUSTABLE UNIVERSAL SURGICAL PLATFORM" by Changquing C. Kao, J. Michael Fitzpatrick, Robert F. Labadie and Peter E. Konrad, which is incorporated herein by reference in its entirety, which itself is a divisional application of, and claims the benefit of U.S. patent application Ser. No. 11/594,700, filed Nov. 7, 2006 and entitled "ADJUSTABLE UNIVERSAL SURGICAL PLATFORM" by Changquing C. Kao, J. Michael Fitzpatrick, Robert F. Labadie, and Peter E. Konrad, which is incorporated by reference herein in its entirety and which itself claims the benefit, pursuant to 35 U.S.C. §119(e), of U.S. provisional patent application Ser. No. 60/734,052, filed Nov. 7, 2005, entitled "ADJUSTABLE UNIVERSAL SURGICAL PLATFORM" by Changquing C. Kao, J. Michael Fitzpatrick, Robert F. Labadie and Peter E. Konrad, which is incorporated herein by reference in its entirety.

FIELD OF THE INVENTION

The present invention generally relates to an apparatus for supporting a surgical platform. More particularly, the present invention relates to a support frame for supporting an adjustable surgical platform.

BACKGROUND OF THE INVENTION

Stereotactic neurosurgery is a field of neurosurgery in which a probe is advanced through a burr hole to a target of interest by means of a mechanical device attached to the skull with aiming based on pre-operative images. The probe may be a biopsy needle or an implantable device, but it is geometrically rigid, so that its tip can be brought to a target of interest specified on a pre-operative image, by means of a geometrical calculation. In the past, large metal frames that encompass the entire head of a patient were used with the attachment of small platforms placed over an entry site. Conventional metal frames are designed for approaching one target at a time with an unrestricted entry point towards the deep target, by employing the principle that the target is at the center of a sphere. Because of the long trajectories involved, both accuracy and patient comfort are challenged by the demands of surgeries for deep brain stimulation (DBS) in which the patients are awake throughout the lengthy surgical procedure.

Other conventional approaches require the attachment of bone-implanted fiducials, the subsequent acquisition of a pre-operative tomogram, and intraoperative optical tracking to aim a probe at its target. However, there are problems regarding geometrically stability, limited space for access to the burr hole and surgical manipulation, which requires a time-consuming process of aiming and locking on the target. Access to the burr hole is crucially important for the purpose of stopping bleeding from the bone cavity, dura, and the surface of the cortex during the procedure. In some conventional devices, a medical professional conducts the aiming process by watching a guiding icon on the screen of the intraoperative tracking system and then locking a guiding platform into place with one hand, while it is held at the correct trajectory with the other hand. The trajectory is two-dimensional, meaning that there are two mutually-perpendicular angular adjustments required, each of which must be set simultaneously for the correct trajectory. Finding the correct trajectory via the guiding icon is time consuming because of the difficulty of making fine adjustments of one angle of the approach without changing the other angle. A further difficulty with this aiming procedure is maintaining both angles of the correct trajectory while locking the device on target. The locking step can be especially frustrating to a medical processional if either angle is changed inadvertently during locking, as revealed by the guiding icon, and as a result, the device must be unlocked and the adjustment started again from the beginning Several iterations may be required, resulting in wasted operating time. In other conventional approaches, a custom apparatus may be built for each particular patient, after preliminary scans of the target area of interest have been taken to obtain specific dimensional and anatomical data for the particular patient. However, following a preliminary scanning procedure, a patient must wait several days or weeks until the custom frame has been built and delivered, and even upon setting up the custom frame in preparation for a surgical procedure, fine-tuning is required to further adjust the apparatus to address intraoperative challenges faced by medical professionals performing the surgical procedure.

Among other needs, there exists a need for adjustable surgical means that can be quickly and accurately configured to provide for varying positions and trajectories for a particular procedure and corresponding particular patient anatomy, and which can intraoperatively guide surgical instruments with accuracy at the desired settings.

Therefore, a heretofore unaddressed need exists in the art to address the aforementioned deficiencies and inadequacies.

SUMMARY OF THE INVENTION

In one aspect, the present invention relates to an apparatus for supporting an adjustable surgical platform. In one embodiment, the apparatus includes a supporting platform portion with a body portion that defines a bore along a central axis A. A plurality of arm portions extend radially from the supporting platform portion around the central axis A, and a plurality of engaging means are positioned on the arm portions. The apparatus also includes a shaft portion extending from the supporting platform portion in a first direction. The shaft portion has a shaft body portion that defines a bore along a longitudinal axis B, that is in communication with the bore of the supporting platform portion. The apparatus further includes a base portion that is connected to the shaft portion. The base portion has a body portion that defines a bore in communication with the bore of the shaft portion and the bore of the supporting platform portion. Mounting means are configured to secure the base portion to a region of interest of a living subject.

In one embodiment, each arm portion has a first end portion connected to the body portion of the supporting platform portion, a second, opposite end portion, and a body portion defined between the first end portion and the second end portion, and at least one of the engaging means is disposed proximate to the second end of a respective at least one of the plurality of arm portions.

In one embodiment, at least one of the arm portions is configured to elevate a respective at least one of the engaging means from the supporting platform portion in a second direction that is substantially opposite the first direction.

In one embodiment, the plurality of engaging means are configured to engage at least a portion of an adjustable surgical platform, and at least one of the engaging means is configured to engage a leg member of the adjustable surgical platform.

In one embodiment, at least one of the engaging means is adjustable in three-dimensions to provide an adjustable positioning angle for an engaged leg member of the adjustable surgical platform.

In one embodiment, the plurality of arm portions are separated at angles $\theta_1$, $\theta_2$, $\theta_3$ from each other around the central axis A, and the angles $\theta_1$, $\theta_2$, $\theta_3$ are the same or different.

In one embodiment, the mounting means includes at least one fastening means configured to secure the base portion to the region of interest of the living subject.

In one embodiment, the apparatus further includes means for securing a surgical tracking instrument to one of the plurality of arm portions.

In another aspect, the present invention relates to a support frame for an adjustable surgical platform. In one embodiment, the support frame includes a supporting platform portion with a body portion that defines a bore between a first end portion and a second, opposite end portion, along a central axis A. A plurality of arm portions extend radially from the supporting platform portion around the central axis A. Each arm portion has a first end portion connected to the body portion of the supporting platform portion, a second, opposite end portion, and a body portion defined between the first end portion and the second end portion. Each of a plurality of engaging means is provided on a respective one of the plurality of arm portions, proximate to the respective second end portion. The support frame also includes a shaft portion extending from the second end portion of the supporting platform portion in a first direction. The shaft portion has a first end portion connected to the body portion of the supporting platform portion, an opposite, second end portion, and a shaft body portion defined between the first end portion and the second end portion. The shaft body portion defines a bore along a longitudinal axis B that is substantially parallel to the central axis A. The bore of the shaft body portion is in communication with the bore defined by the supporting platform portion. The support frame further includes a base portion that is connected to the second end portion of the shaft portion. The base portion has a first end portion and an opposite, second end portion that define a body portion between them. The body portion defines a bore that is in communication with the bore defined by the shaft portion and the bore defined by the supporting platform portion. The support frame further includes mounting means that are configured to mount the base portion to the skull of a living subject.

In one embodiment, each of the arm portions is configured to elevate a respective one of the engaging means from the body portion of the supporting platform portion, in a second direction that is substantially opposite the first direction.

In one embodiment, each of the plurality of engaging means is configured to engage respective leg member of the adjustable surgical platform, and the engaging means of each of the arm portions is adjustable in three-dimensions to provide an adjustable positioning angle for corresponding engaged leg members of an adjustable surgical platform.

In one embodiment, each of the plurality of engaging means is configured to engage a ball portion of a respective leg member of the adjustable surgical platform.

In one embodiment, each of the engaging means includes a concave recess.

In one embodiment, the plurality of arm portions are separated at equal angles $\theta_1$, $\theta_2$, $\theta_3$ from each other around the central axis A.

In one embodiment, the plurality of arm portions includes three arm portions separated 120° from each other around the central axis A.

In one embodiment, the mounting means include at least one fastening means configured to secure the base portion of the support frame to the skull of the living subject.

In one embodiment, the support frame further includes a means for securing a surgical tracking instrument to one of the plurality of arm portions.

In yet another aspect, the present invention relates to a support frame for an adjustable surgical platform. In one embodiment, the support frame includes a supporting platform portion with an annular body portion defining a bore between a first end portion and second, opposite end portion, along a central axis A. A plurality of arm portions extend radially from the annular body portion around the central axis A, and each arm portion has a first end portion connected to the annular body portion, a second, opposite end portion, and a body portion defined between the first end portion and the second end portion. The support frame further includes a plurality of engaging means, each positioned on a respective one of the arm portions proximate to the second end portion. Each of the engaging means is configured to engage a corresponding leg member of an adjustable surgical platform. The support frame further includes a shaft portion extending from the second end portion of the annular body portion in a first direction. The shaft portion has a first end portion connected to the annular body portion, an opposite, second end portion, and a body portion defined between the first end portion and the second end portion. The body portion defines a bore along a longitudinal axis B that is substantially parallel to the central axis A. The bore of the shaft portion is in communication with the bore defined by the supporting platform portion. The support frame further includes a base portion connected to the second end of the shaft portion. The base portion has a first end portion and an opposite, second end portion that defines a body portion between them, and the body portion defines a bore that is in communication with the bore defined by the shaft portion and the bore defined by the supporting platform portion. The support frame further includes mounting means configured to mount the base portion to the skull of a living subject.

In one embodiment, each of the arm portions is configured to elevate a respective one of the engaging means from the body portion of the supporting platform portion in a second direction that is substantially opposite the first direction.

In one embodiment, each of the engaging means is adjustable in three-dimensions to provide an adjustable positioning angle for a corresponding engaged leg member of the adjustable surgical platform.

In one embodiment, the plurality of arm portions includes three arm portions separated 120° from each other around the central axis A.

In one embodiment, the mounting means includes at least one fastening means configured to secure the base portion to the skull of the living subject.

In one embodiment, the support frame further includes means for securing a surgical tracking instrument to one of the plurality of arm portions.

In yet another aspect, the present invention relates to an apparatus for supporting an adjustable surgical platform. In one embodiment, the apparatus includes a supporting platform portion with a body portion that defines a bore along a central axis. A plurality of arm portions extend radially from the supporting platform portion around the central axis, and a plurality of engaging means are positioned on the arm portions. Mounting means are configured to secure the supporting platform portion to a region of interest of a living subject.

In one embodiment, each arm portion has a first end portion connected to the body portion of the supporting platform portion, a second, opposite end portion, and a body portion defined between the first end portion and the second end portion, and at least one of the engaging means is disposed proximate to the second end of a respective at least one of the plurality of arm portions.

In one embodiment, at least one of the arm portions is configured to elevate a respective at least one of the engaging means from the supporting platform portion.

In one embodiment, the plurality of engaging means are configured to engage at least a portion of an adjustable surgical platform, and at least one of the engaging means is configured to engage a leg member of the adjustable surgical platform.

In one embodiment, at least one of the engaging means is adjustable in three-dimensions to provide an adjustable positioning angle for an engaged leg member of the adjustable surgical platform.

In one embodiment, the plurality of arm portions are separated at angles $\theta_1$, $\theta_2$, $\theta_3$ from each other around the central axis, and the angles $\theta_1$, $\theta_2$, $\theta_3$ are the same or different.

In one embodiment, the mounting means includes at least one fastening means configured to secure the supporting platform portion to the region of interest of the living subject.

In one embodiment, the apparatus further includes means for securing a surgical tracking instrument to one of the plurality of arm portions.

In yet another aspect, the present invention relates to a support frame for an adjustable surgical platform. In one embodiment, the support frame includes a supporting platform portion with a body portion that defines a bore between a first end portion and a second, opposite end portion, along a central axis. A plurality of arm portions extend radially from the supporting platform portion around the central axis. Each arm portion has a first end portion connected to the body portion of the supporting platform portion, a second, opposite end portion, and a body portion defined between the first end portion and the second end portion. Each of a plurality of engaging means is provided on a respective one of the plurality of arm portions, proximate to the respective second end portion. The support frame further includes mounting means that are configured to mount the supporting platform portion to the skull of a living subject.

In one embodiment, each of the arm portions is configured to elevate a respective one of the engaging means from the body portion of the supporting platform portion.

In one embodiment, each of the plurality of engaging means is configured to engage respective leg member of the adjustable surgical platform, and the engaging means of each of the arm portions is adjustable in three-dimensions to provide an adjustable positioning angle for corresponding engaged leg members of an adjustable surgical platform.

In one embodiment, each of the plurality of engaging means is configured to engage a ball portion of a respective leg member of the adjustable surgical platform.

In one embodiment, each of the engaging means includes a concave recess.

In one embodiment, the plurality of arm portions are separated at equal angles $\theta_1$, $\theta_2$, $\theta_3$ from each other around the central axis.

In one embodiment, the plurality of arm portions includes three arm portions separated 120° from each other around the central axis.

In one embodiment, the mounting means include at least one fastening means configured to secure the supporting platform portion to the skull of the living subject.

In one embodiment, the support frame further includes a means for securing a surgical tracking instrument to one of the plurality of arm portions.

In yet another aspect, the present invention relates to a support frame for an adjustable surgical platform. In one embodiment, the support frame includes a supporting platform portion with an annular body portion defining a bore between a first end portion and second, opposite end portion, along a central axis. A plurality of arm portions extend radially from the annular body portion around the central axis, and each arm portion has a first end portion connected to the annular body portion, a second, opposite end portion, and a body portion defined between the first end portion and the second end portion. The support frame further includes a plurality of engaging means, each positioned on a respective one of the arm portions proximate to the second end portion. Each of the engaging means is configured to engage a corresponding leg member of an adjustable surgical platform. The support frame further includes mounting means configured to mount the supporting platform portion to the skull of a living subject.

In one embodiment, each of the arm portions is configured to elevate a respective one of the engaging means from the body portion of the supporting platform portion.

In one embodiment, each of the engaging means is adjustable in three-dimensions to provide an adjustable positioning angle for a corresponding engaged leg member of the adjustable surgical platform.

In one embodiment, the plurality of arm portions includes three arm portions separated 120° from each other around the central axis.

In one embodiment, the mounting means includes at least one fastening means configured to secure the supporting platform portion to the skull of the living subject.

In one embodiment, the support frame further includes means for securing a surgical tracking instrument to one of the plurality of arm portions.

BRIEF DESCRIPTION OF THE DRAWINGS

The accompanying drawings illustrate one or more embodiments of the invention and, together with the written description, serve to explain various aspects and principles of the invention. Wherever possible, the same reference numbers are used throughout the drawings to refer to the same or like elements of an embodiment, and wherein.

DETAILED DESCRIPTION OF THE INVENTION

Figure 1A:
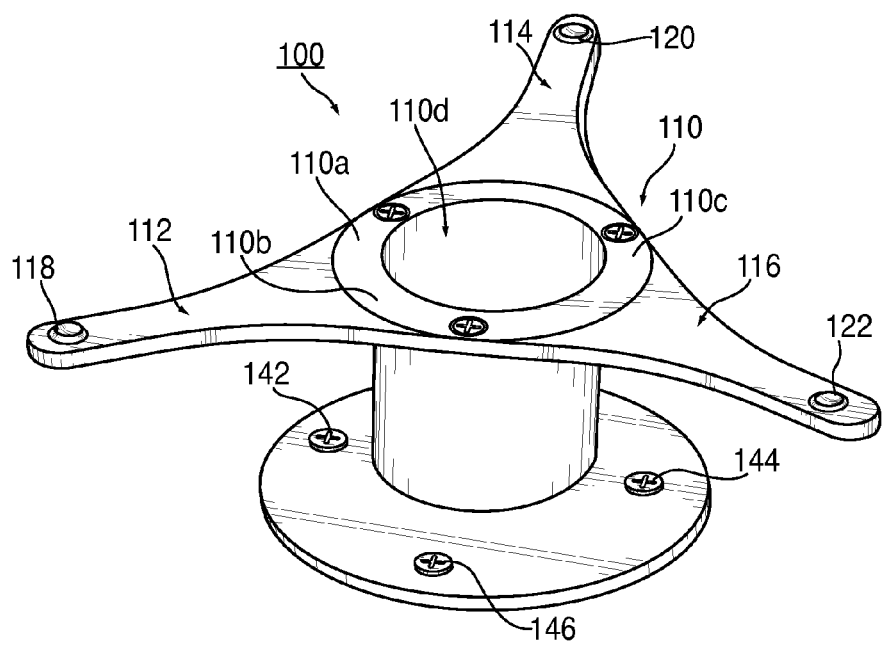
FIG. 1A schematically shows a perspective view of a support frame according to one exemplary embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing rat, monkey or the like.

The description will be made as to the embodiments of the present invention in conjunction with the accompanying drawings in FIGS. 1-8.

Now referring to exemplary embodiments shown in FIGS. 1-8, in one aspect, the present invention relates to an apparatus 100 for supporting an adjustable surgical platform. In one embodiment, the apparatus includes a supporting platform portion 110 with a body portion 110c that defines a bore 110d along a central axis A. A plurality of arm portions 112, 114, 116 extend radially from the supporting platform portion 110 around the central axis A, and a plurality of engaging means 118, 120, 122 are positioned on respective arm portions 112, 114, 116. Each of the arm portions 112, 114, 116 has a first end portion 112a, 114a, 116a connected to the body portion 110c of the supporting platform portion 110, a second, opposite end portion 112b, 114b, 116b, and a body portion 112c, 114c, 116c defined between the first end portion 112a, 114a, 116a and second end portion 112b, 114b, 116b, respectively. The apparatus 100 also includes a shaft portion 130 extending from the supporting platform portion 110 in a first direction, with a shaft body portion 130c that defines a bore 130d along a longitudinal axis B. The bore 130d of the shaft body portion 130 is in communication with the bore 110d of the supporting platform portion 110. The apparatus 100 further includes a base portion 140 that is connected to the shaft portion 130. The base portion 140 has a first end portion 140a, a second, opposite second portion 140b, and a body portion 140c defined between the first end portion 140a and the second end portion. The body portion 140c defines a bore 140d that is in communication with the bore 130d of the shaft portion 130 and the bore 110d of the supporting platform portion 110. Mounting means 142, 144, 146 are configured to secure the base portion 140 to a region of interest 150 of a living subject.

In one embodiment, at least one of the engaging means 118, 120, 122 is disposed proximate the second end 112b, 114b, 116b of a respective at least one of the plurality of arm portions 112, 114, 116.

In one embodiment, at least one of the arm portions 312, 314, 316 is configured to elevate a respective at least one of the engaging means 318, 320, 322 from the supporting platform portion 310 in a second direction that is substantially opposite the first direction.

In one embodiment, the engaging means 118, 120, 122 are configured to engage at least a portion 216, 218, 220 of an adjustable surgical platform 200, which as shown corresponds to a leg member 210, 212, 214 of the adjustable surgical platform 200. In this embodiment, at least one of the engaging means 118, 120, 122 is adjustable in three-dimensions to provide an adjustable positioning angle for an engaged leg member 210, 212, 214 of the adjustable surgical platform 200.

In one embodiment, the arm portions 112, 114, 116 are separated at angles $\theta_1$, $\theta_2$, $\theta_3$ from each other around the central axis A. The angles $\theta_1$, $\theta_2$, $\theta_3$ can be the same or different from each other.

In one embodiment, the mounting means 142, 144, 146 includes at least one fastening means 142, 144, 146 configured to secure the base portion 140 to the region of interest 150 of the living subject.

In one embodiment, a means 402 (or 502) is configured for securing a surgical tracking instrument 430 to one of the plurality of arm portions 112, 114, 116.

In another aspect, the present invention relates to a support frame 100 for an adjustable surgical platform 200. In one embodiment, the support frame includes a supporting platform portion 110 with a body portion 110c that defines a bore 110d between a first end portion 110a and a second, opposite end portion 110b, along a central axis A. A plurality of arm portions 112, 114, 116 extend radially from the body portion 110c around the central axis A. Each of the arm portions 112, 114, 116 has a first end portion 112a, 114a, 116a connected to the body portion 110c of the supporting platform portion 110, a second, opposite end portion 112b, 114b, 116b, and a body portion 112c, 114c, 116c defined between them, respectively. A plurality of engaging means 118, 120, 122 are each positioned on respective one of the arm portions 112, 114, 116, proximate to the respective second end portions 112b, 114b, 116b of the arm portions 112, 114, 116.

The support frame 100 also includes a shaft portion 130 that extends from the second end portion 110b of the supporting platform portion 110 in a first direction. The shaft portion 130 has a first end portion 130a connected to the body portion 110c of the supporting platform portion 110, an opposite, second end portion 130b, and a shaft body portion 130c that is defined between the first end portion 130a and the second end portion 130b. The shaft body portion 130c defines a bore 130d along a longitudinal axis B, and the bore 130b of the shaft body portion 130c is in communication with the bore 110d of the supporting platform portion 110. The longitudinal axis B is substantially parallel to the central axis A. The support frame 100 further includes a base portion 140 that is connected to the second end portion 130b of the shaft portion 130. The base portion 140 has a first end portion 140a and a second, opposite end portion 140b that define a body portion 140c between them, and the body portion 140c defines a bore 140d that is in communication with the bore 130d of the shaft portion 130 and the bore 110d of the supporting platform portion 110. The support frame 100 also includes mounting means 142, 144, 146 that are configured to mount the base portion 140 to the skull 150 of a living subject.

In one embodiment, each of the arm portions 312, 314, 316 is configured to elevate a respective one of the engaging means 318, 320, 322 from the body portion 310c of the supporting platform portion 310 in a second direction that is substantially opposite the first direction.

In one embodiment, each of the engaging means 118, 120, 122 is configured to engage a leg member 210, 212, 214 of the adjustable surgical platform 200. In this embodiment, each of the engaging means 118, 120, 122 corresponding to each of the respective arm portions 112, 114, 116 is adjustable in three-dimensions, to provide an adjustable positioning angle for corresponding engaged leg members 210, 212, 214 of an adjustable surgical platform 200. Each of the engaging means 118, 120, 122 is configured to engage a ball portion 216, 218, 220 of a respective leg member 210, 212, 214 of the adjustable surgical platform 200.

In one embodiment, each of the engaging means 118, 120, 122 has a socket-ball joint.

In one embodiment, each of the engaging means 118, 120, 122 has a respective concave recess 119, 121, 123.

In one embodiment, the arm portions 112, 114, 116 are separated at equal angles $\theta_1$, $\theta_2$, $\theta_3$ from each other around the central axis A. In this embodiment, the three arm portions 112, 114, 116 are separated 120° from each other around the central axis A.

In one embodiment, the mounting means 142, 144, 146 has at least one fastening means 142, 144, 146 configured to secure the base portion 140 to the skull 150 of the living subject.

In one embodiment, the support frame 100 further includes a means 402 (or 502) for securing a surgical tracking instrument 430 to one of the arm portions 412, 414, 416.

In yet another aspect, the present invention relates to a support frame 100 for an adjustable surgical platform 200. In one embodiment, the supporting platform portion 110 has an annular body portion 110c that defines a bore 110d between a first end portion 110a and a second, opposite end portion 110b, along a central axis A. A plurality of arm portions 112, 114, 116 extend radially from the annular body portion 110c around the central axis A, and each arm portion 112, 114, 116 has a first end portion 112a, 114a, 116a connected to the annular body portion 110c, a second, opposite end portion 112b, 114b, 116b, and a body portion 112c, 114c, 116c defined between the first end portion 112a, 114a, 116a and the second end portion 112b, 114b, 116b, respectively. The support frame 100 also includes a plurality of engaging means 118, 120, 122 that are each positioned on a respective one of the arm portions 112, 114, 116, proximate to the respective second end portion 112b, 114b, 116 and configured to engage a corresponding leg member 210, 212, 214 of an adjustable surgical platform 200.

The support frame 100 also includes a shaft portion 130 extending from the second end portion 110b of the annular body portion 110c in a first direction. The shaft portion 130 has a first end portion 130a connected to the annular body portion 110c, an opposite, second end portion 130b, and a body portion 130c defined between the first end portion 130a and second end portion 130b. The body portion 130c defines a bore 130d along a longitudinal axis B. The longitudinal axis is substantially parallel to the central axis A. The bore 130d is in communication with the bore 110d defined by the supporting platform portion 110.

The support frame 100 further includes a base portion 140 that is connected to the second end 130b of the shaft portion 130. The base portion 140 has a first end portion 140a and an opposite, second end portion 140b that define a body portion 140c between them. The body portion 140c is in communication with the bore 130d of the shaft portion 130 and the bore 110d of the supporting platform portion 110. The support frame 100 further includes means 142, 144, 146 that are configured to mount the base portion 140 to the skull 150 of a living subject.

In one embodiment, each of the arm portions 312, 314, 316 is configured to elevate a respective one of the engaging means 318, 320, 322 from the body portion 310c of the supporting platform portion 310 in a second direction that is substantially opposite the first direction.

In one embodiment, each of the engaging means 118, 120, 122 is adjustable in three-dimensions to provide an adjustable positioning angle for a corresponding engaged leg member 210, 212, 214 of the adjustable surgical platform 200.

In one embodiment, the plurality of arm portions 112, 114, 116 includes three arm portions 112, 114, 116 that are separated 120° from each other around the central axis A.

In one embodiment, the mounting means 142, 144, 146 has at least one fastening means 142, 144, 146 configured to secure the base portion 140 to the skull 150 of the living subject.

In one embodiment, the support frame 100 further includes a means 402 (or 502) for securing a surgical tracking instrument 430 to one of the arm portions 412, 414, 416.

In yet another aspect, the present invention relates to an apparatus 600 for supporting an adjustable surgical platform 200. In one embodiment, the apparatus 600 includes a supporting platform portion 610 with a body portion 610c that defines a bore 610d along a central axis. A plurality of arm portions 612, 614, 616 extend radially from the supporting platform portion 610 around the central axis, and a plurality of engaging means 618, 620, 622 are positioned on respective arm portions 612, 614, 616. Each of the arm portions 612, 614, 616 has a first end portion 612a, 614a, 616a connected to the body portion 610c of the supporting platform portion 610, a second, opposite end portion 612b, 614b, 616b, and a body portion 612c, 614c, 616c defined between the first end portion 612a, 614a, 616a and second end portion 612b, 614b, 616b, respectively. Mounting means 611, 613, 615 are configured to secure the supporting platform portion 610 to a region of interest 150 of a living subject.

In one embodiment, at least one of the engaging means 618, 620, 622 is disposed proximate the second end 612b, 614b, 616b of a respective at least one of the plurality of arm portions 612, 614, 616.

In one embodiment, at least one of the arm portions 612, 614, 616 is configured to elevate a respective at least one of the engaging means 618, 620, 622 from the supporting platform portion (see FIG. 8 embodiment with arm portions 812, 814, 816 configured to elevate engaging means 818, 820, 822 from supporting platform portion 810).

Figure 7A:
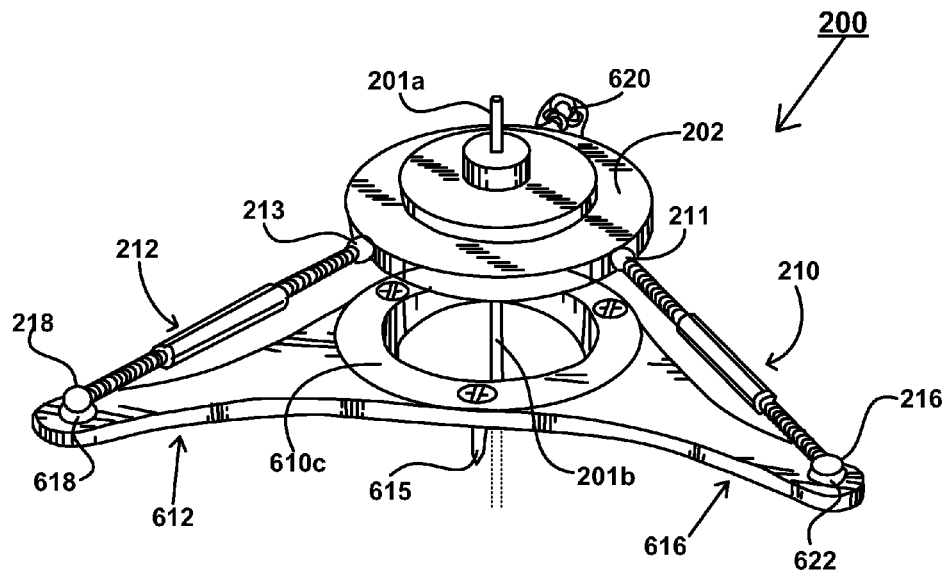
FIG. 7A schematically shows perspective view of a support frame according to the exemplary embodiment shown in FIGS. 6A and 6B, supporting an adjustable surgical platform.
Figure 7B:
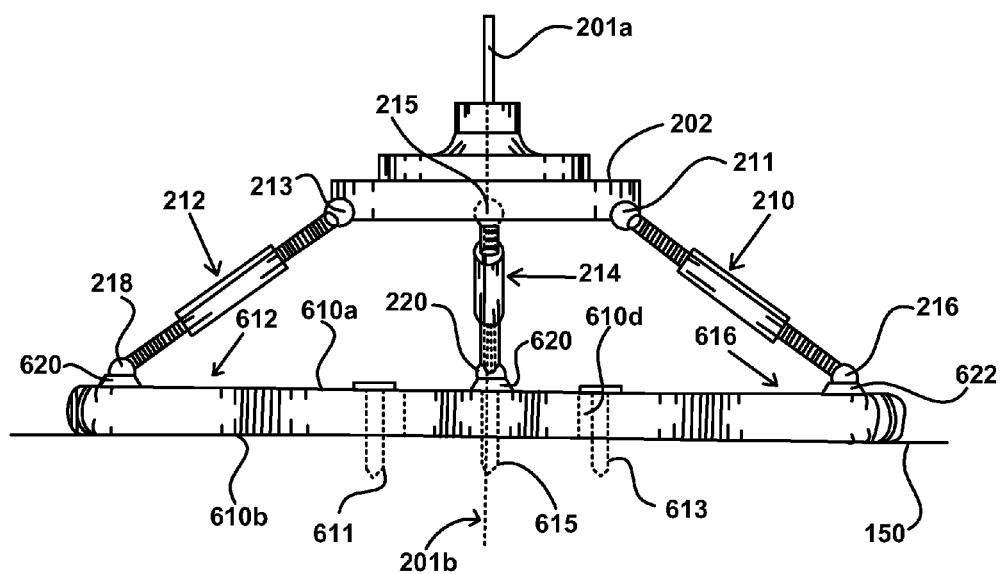
FIG. 7B schematically shows a side view of the support frame shown in FIG. 7A, supporting an adjustable surgical platform.

In one embodiment, the engaging means 618, 620, 622 are configured to engage at least a portion 216, 218, 220 of an adjustable surgical platform 200, which as shown in FIGS. 7A and 7B corresponds to a leg member 210, 212, 214 of the adjustable surgical platform 200. In this embodiment, at least one of the engaging means 618, 620, 622 is adjustable in three-dimensions to provide an adjustable positioning angle for an engaged leg member 210, 212, 214 of the adjustable surgical platform 200.

In one embodiment, the arm portions 612, 614, 616 are separated at angles $\theta_1$, $\theta_2$, $\theta_3$ from each other around the central axis. The angles $\theta_1$, $\theta_2$, $\theta_3$ can be the same or different from each other.

In one embodiment, the mounting means 611, 613, 615 includes at least one fastening means configured to secure the supporting platform portion 610 to the region of interest 150 of the living subject.

In yet another aspect, the present invention relates to a support frame 600 for an adjustable surgical platform 200. In one embodiment, the support frame 600 includes a supporting platform portion 610 with a body portion 610c that defines a bore 610d between a first end portion 610a and a second, opposite end portion 610b, along a central axis. A plurality of arm portions 612, 614, 616 extend radially from the body portion 610c around the central axis. Each of the arm portions 612, 614, 616 has a first end portion 612a, 614a, 616a connected to the body portion 610c of the supporting platform portion 110, a second, opposite end portion 612b, 614b, 616b, and a body portion 612c, 614c, 616c defined between them, respectively. A plurality of engaging means 618, 620, 622 are each positioned on respective one of the arm portions 612, 614, 616, proximate to the respective second end portions 612b, 614b, 616b of the arm portions 612, 614, 616.

The support frame 600 also includes mounting means 611, 613, 614 that are configured to mount the supporting platform portion 610 to the skull 150 of a living subject.

In one embodiment, each of the arm portions 612, 614, 616 is configured to elevate a respective at least one of the engaging means 618, 620, 622 from the supporting platform portion (see FIG. 8 embodiment with arm portions 812, 814, 816 configured to elevate engaging means 818, 820, 822 from supporting platform portion 810).

In one embodiment, each of the engaging means 618, 620, 622 is configured to engage a leg member 210, 212, 214 of the adjustable surgical platform 200. In this embodiment, each of the engaging means 618, 620, 622 corresponding to each of the respective arm portions 612, 614, 616 is adjustable in three-dimensions, to provide an adjustable positioning angle for corresponding engaged leg members 210, 212, 214 of the adjustable surgical platform 200. Each of the engaging means 618, 620, 622 is configured to engage a ball portion 216, 218, 220 of a respective leg member 210, 212, 214 of the adjustable surgical platform 200.

In one embodiment, each of the engaging means 618, 620, 622 has a socket-ball joint.

In one embodiment, each of the engaging means 618, 620, 622 has a concave recess 619, 621, 623.

In one embodiment, the arm portions 612, 614, 616 are separated at equal angles $\theta_1$, $\theta_2$, $\theta_3$ from each other around the central axis. In this embodiment, the three arm portions 612, 614, 616 are separated 120° from each other around the central axis.

In one embodiment, the mounting means 611, 613, 615 has at least one fastening means configured to secure the supporting platform portion 610 to the skull 150 of the living subject.

In yet another aspect, the present invention relates to a support frame 600 for an adjustable surgical platform 200. In one embodiment, the supporting platform portion 610 has an annular body portion 610c that defines a bore 610d between a first end portion 610a and a second, opposite end portion 610b, along a central axis. A plurality of arm portions 612, 614, 616 extend radially from the annular body portion 610c around the central axis, and each arm portion 612, 614, 616 has a first end portion 612a, 614a, 616a connected to the annular body portion 610c, a second, opposite end portion 612b, 614b, 616b, and a body portion 612c, 614c, 616c defined between the first end portion 612a, 614a, 616a and the second end portion 612b, 614b, 616b, respectively. The support frame 600 also includes a plurality of engaging means 618, 620, 622 that are each positioned on a respective one of the arm portions 612, 614, 616, proximate to the respective second end portion 612b, 614b, 616 and configured to engage a corresponding leg member 210, 212, 214 of an adjustable surgical platform 200.

The support frame 600 further includes means 611, 613, 615 that are configured to mount the supporting platform portion 610 to the skull 150 of a living subject.

In one embodiment, each of the arm portions is configured to elevate a respective one of the engaging means from the supporting platform portion (see FIG. 8 embodiment with arm portions 812, 814, 816 configured to elevate engaging means 818, 820, 822 from supporting platform portion 810).

In one embodiment, each of the engaging means 618, 620, 622 is adjustable in three-dimensions to provide an adjustable positioning angle for a corresponding engaged leg member 210, 212, 214 of the adjustable surgical platform 200.

In one embodiment, the plurality of arm portions 612, 614, 616 includes three arm portions that are separated 120° from each other around the central axis.

In one embodiment, the mounting means 611, 613, 615 has at least one fastening means configured to secure the supporting platform portion 610 to the skull 150 of the living subject.

Figure 1B:
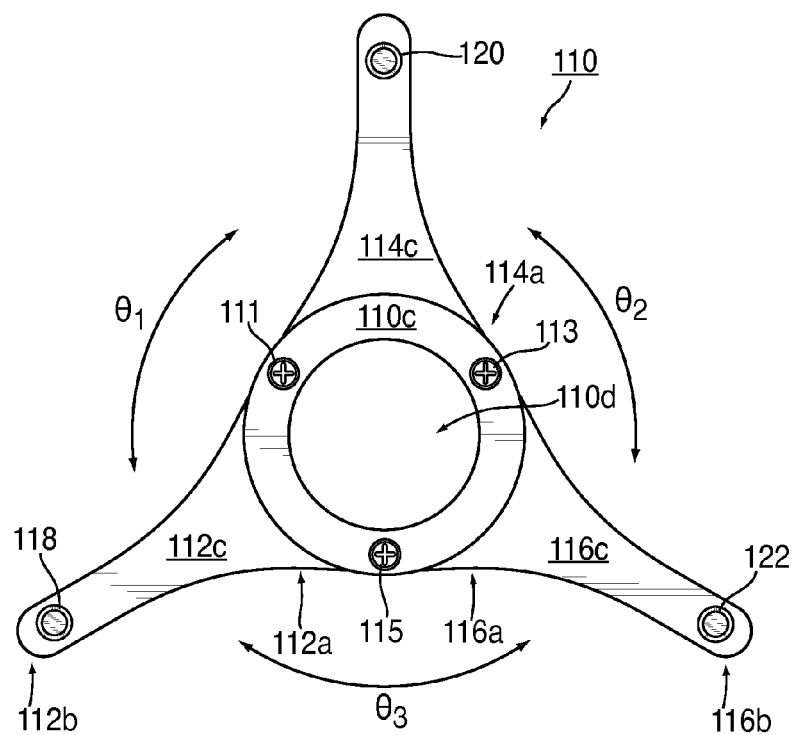
FIG. 1B schematically shows a top view of the surgical platform portion and arm portions of the support frame shown in FIG. 1A.
Figure 1C:
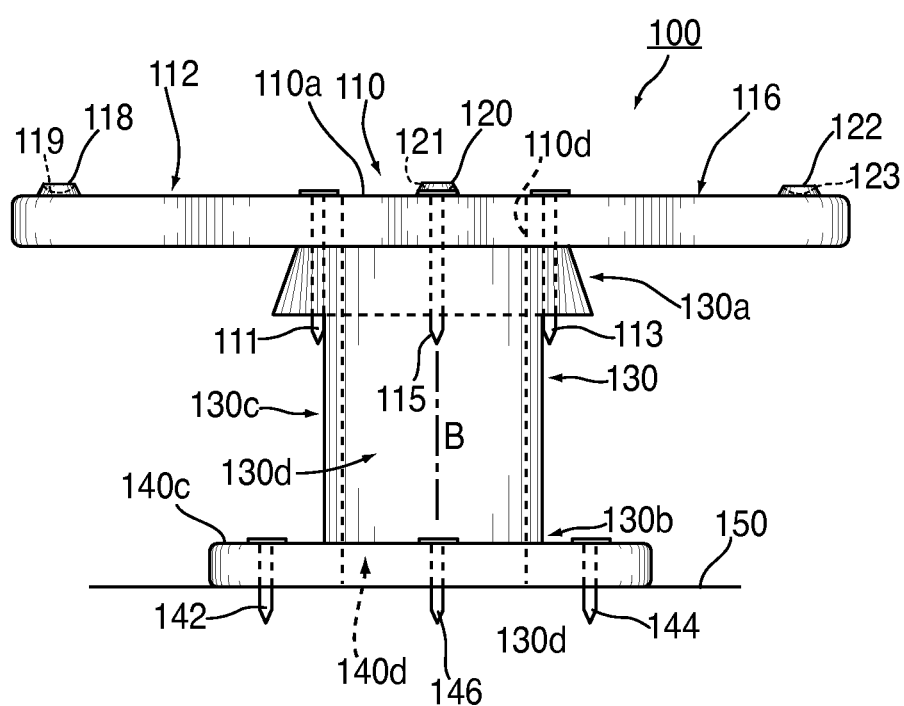
FIG. 1C schematically shows a side view of the support frame shown in FIGS. 1A and 1B.

Now referring specifically to FIGS. 1A, 1B, and 1C, a support frame 100 is shown, according to one exemplary embodiment of the present invention. Particularly, FIG. 1A provides a perspective view of the support frame 100, FIG. 1B provides a top view of the supporting platform portion 110 of the support frame 100, and FIG. 1C provides a side view of the support frame 100. As shown, the support frame includes a supporting platform portion 110 with a substantially annular body portion 110c that defines a bore 110d between a first end portion 110a and a second, opposite end portion 110b, along a central axis A. A plurality of arm portions 112, 114, 116 extend radially from the supporting platform portion 110 around the central axis A, and are separated from each other by angles $\theta_1$, $\theta_2$, $\theta_3$, which are each about 120°. Each of the arm portions 112, 114, 116 has a first end portion 112a, 114a, 116a connected to the body portion 110c of the supporting platform portion 110, a second, opposite end portion 112b, 114b, 116b, and a body portion 112c, 114c, 116c defined between the first end portion 112a, 114a, 116 and second end portion 112b, 114b, 116b, respectively. A plurality of engaging means 118, 120, 122 are each positioned on respective one of the arm portions 112, 114, 116, proximate to the respective second end portions 112b, 114b, 116b of the arm portions 112, 114, 116. Fastening means 111, 113, 115 such as mounting screws, bolts, or pins are provided through the body portion 110c of the supporting platform portion 110, to securely attach the body portion 110c to the shaft portion 130 at the first end 130a.

As will be discussed in more detail below with reference to FIGS. 4A, 4B, in one embodiment, the support frame 100 further includes a means 402 for securing a surgical tracking instrument 430 to one or more of the arm portions, shown in this embodiment as provided on an arm portion 512. FIG. 5 shows an alternative embodiment that includes a means 502 for securing the surgical tracking instrument 430 to one of the arm portions.

The support frame 100 also includes a shaft portion 130 that extends from the second end portion 110b of the supporting platform portion 110. The shaft portion 130 has a first end portion 130a connected to the body portion 110c of the supporting platform portion 110, an opposite, second end portion 130b, and a shaft body portion 130c that is defined between the first end portion 130a and the second end portion 130b. The shaft body portion 130c defines a bore 130d, along a longitudinal axis B that is substantially parallel to the central axis A. The bore 130b of the shaft body portion 130c is in communication with the bore 110d defined by the supporting platform portion 110.

A base portion 140 is also included in the support frame 100. The base portion 140 is connected to the second end portion 130b of the shaft portion 130, and has a first end portion 140a and a second, opposite end portion 140b that define a body portion 140c between them. The body portion 140c defines a bore 140d that is in communication with the bore 130d defined by the shaft portion 130 and the bore 110d of the supporting platform portion 110. The support frame also includes mounting means 142, 144, 146 such as mounting screws, pins, rods, bolts, and/or other types of anchoring mechanisms that are configured to securely mount the base portion 140 to the skull 150 of a living subject.

Figure 2A:
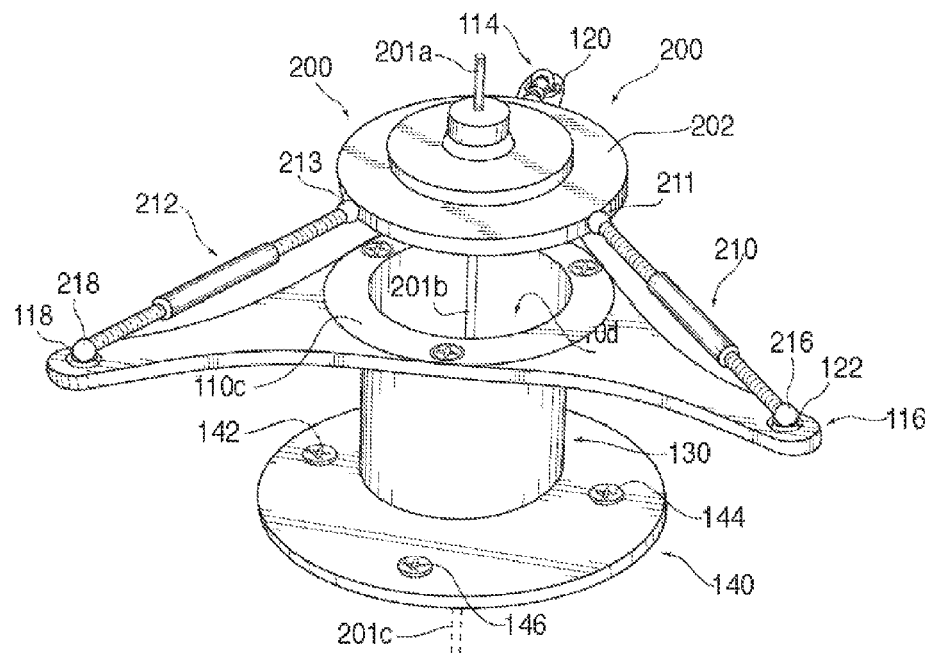
FIG. 2A schematically shows perspective view of a support frame according to the exemplary embodiment shown in FIGS. 1A, 1B, and 1C, supporting an adjustable surgical platform.
Figure 2B:
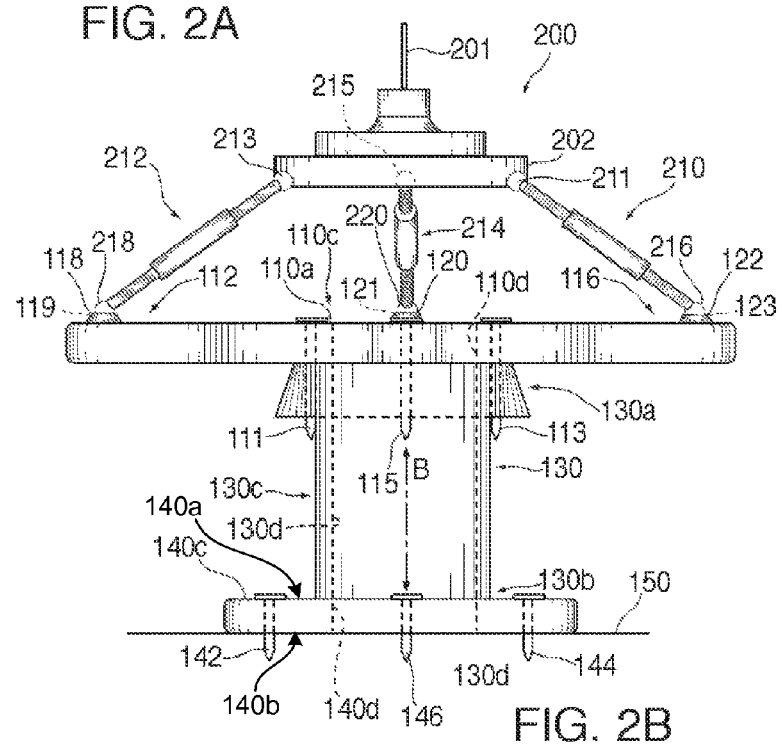
FIG. 2B schematically shows a side view of the support frame shown in FIG. 2A, supporting the adjustable surgical frame shown in FIG. 2A.

Now referring also to the exemplary embodiment shown in FIGS. 2A and 2B, each of the engaging means 118, 120, 122 is configured to engage a leg member 210, 212, 214 of an adjustable surgical platform 200. In this embodiment, the engaging means 118, 120, 122 of each of the arm portions 112, 114, 116 is adjustable in three-dimensions to provide an adjustable positioning angle for corresponding engaged leg members 210, 212, 214 of an adjustable surgical platform 200. Each of the engaging means 118, 120, 122 has a socket-ball joint with a respective concave recess 119, 121, 123 configured to receive a respective ball portion 216, 218, and 220 of a respective one of a plurality of leg members 210, 212, and 214 of the adjustable surgical platform 200. It should be appreciated that other engaging means may be used without departing from the scope of the present invention according to aspects disclosed herein. For example, other types of mechanical joints or interfaces may be used to provide for rotational or other movement for adjustment of a surgical platform in connection with one or more leg members of the adjustable surgical platform.

Now referring specifically to the exemplary embodiments of FIGS. 2A and 2B, FIG. 2A schematically shows perspective view of a support frame 100 according to the exemplary embodiment shown in FIGS. 1A, 1B, and 1C, supporting an adjustable surgical platform 200, and FIG. 2B schematically shows a side view of the support frame 100 according to the exemplary embodiment shown in FIG. 2A, supporting the adjustable surgical frame 200 shown in FIG. 2A. The adjustable surgical platform 200 has a probe 201a, 201b, 201c guided on a trajectory through a bore (not shown) of a body portion 202 of the adjustable surgical platform 200. An example of a suitable body portion with a ball joint for positioning the probe can be found in U.S. patent application Ser. No. 11/594,700, which is incorporated by reference herein in its entirety. The trajectory continues through the bore 110d defined by the body portion 110c of the support platform portion 110, through the bore 130d of the shaft portion, and through the bore 140d of the base portion 140 to a target area of a living subject located inside the skull 150 of a living subject. For example, the probe 201a, 201b may provide an electrical stimulation lead with an electrode for deep brain stimulation (DBS) or include a biopsy needle. The leg members 210, 212, 214 connect to the body portion 202 of the adjustable surgical platform 200 at connections 211, 213, 215 and have respective ball portions 216, 218, 220 for engaging with the engaging means 118 and 122 disposed on arm portions 116 and 118 of the support platform portion 110.

Figure 3A:
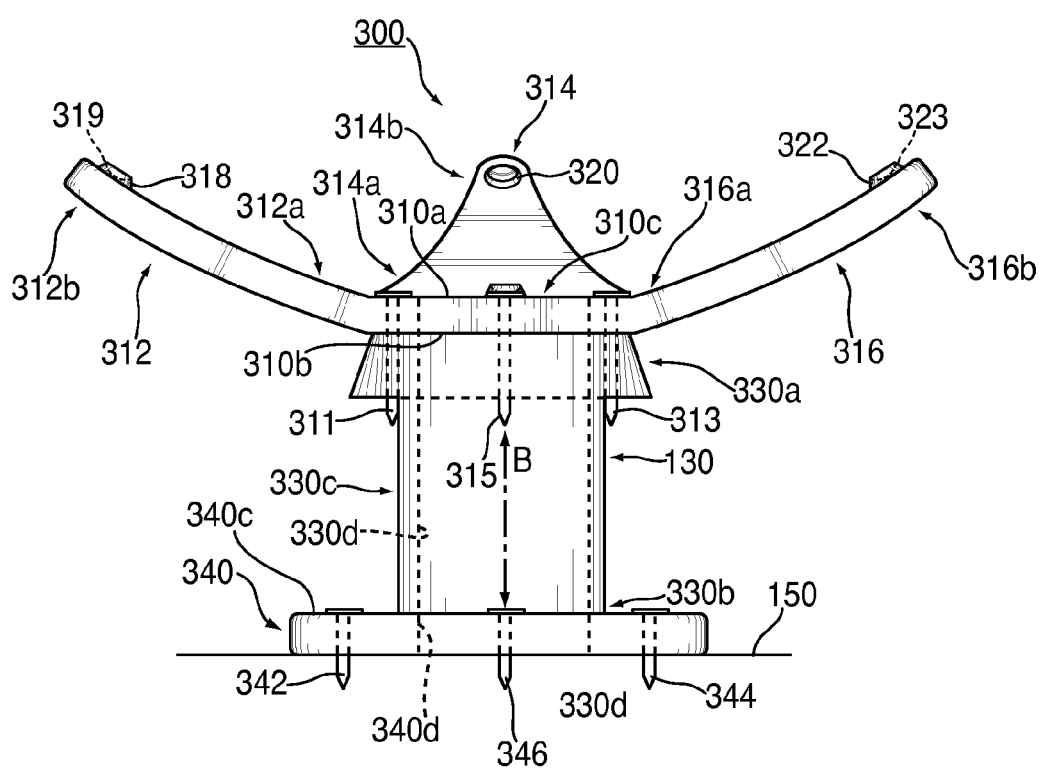
FIG. 3A schematically shows a side view of a support frame according to one exemplary embodiment of the present invention.
Figure 3B:
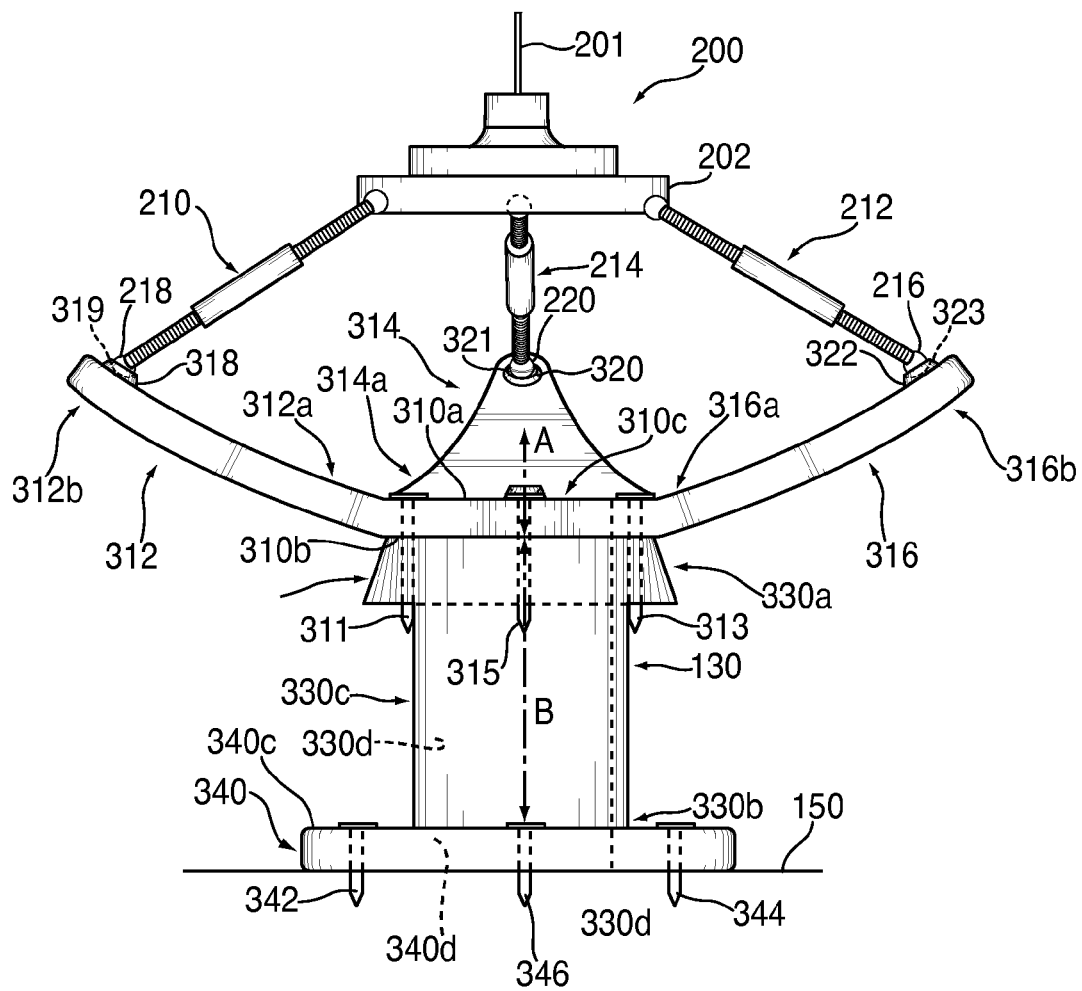
FIG. 3B schematically shows a side view of the support frame shown in FIG. 3A, supporting an adjustable surgical platform.

Now referring specifically to FIGS. 3A and 3B, FIG. 3A schematically shows a side, cross-sectional view of a support frame 300 according to one exemplary embodiment of the present invention, and FIG. 3B schematically shows a side, cross-sectional view of the support frame 300 shown in FIG. 3A, supporting an adjustable surgical platform 200. As shown, the support frame includes a supporting platform portion 310 with a substantially annular body portion 310c that defines a bore 310d between a first end portion 310a and a second, opposite end portion 310b, along a central axis A. A plurality of arm portions 312, 314, 316 extend radially from the supporting platform portion 310 around the central axis A, separated from each other by angles $\theta_1$, $\theta_2$, $\theta_3$, which are each about 120°. Each of the arm portions 312, 314, 316 has a respective first end portion 312a, 314a, 316a connected to the body portion 310c of the supporting platform portion 310, a second, opposite end portion 312b, 314b, 316b, and a body portion 312c, 314c, 316c defined between the first end portion 312a, 314a, 316a and the second end portion 312b, 314b, 316b, respectively. A plurality of engaging means 318, 320, 322 are each positioned on respective one of the arm portions 312, 314, 316, proximate to the respective second end portions 312b, 314b, 316b of the arm portions 312, 314, 316. Fastening means 311, 313, 315 such as mounting screws, bolts, or pins are provided through the body portion 310c of the supporting platform portion, to securely attach the body portion 310c to the shaft portion 330 at the first end 330a.

The support frame 300 also includes a shaft portion 330 that extends from the second end portion 310b of the supporting platform portion 310. The shaft portion 330 has a first end portion 330a connected to the body portion 310c of the supporting platform portion 310, an opposite, second end portion 330b, and a shaft body portion 330c that is defined between the first end portion 330a and the second end portion 330b. The shaft body portion 330c defines a bore 330d, along a longitudinal axis B that is substantially parallel to the central axis A. The bore 330b of the shaft body portion 330c is in communication with the bore 310d defined by the supporting platform portion 310.

A base portion 340 is also included in the support frame 300. The base portion 340 is connected to the second end portion 330b of the shaft portion 330, and has a first end portion 340a and a second, opposite end portion 340b that define a body portion 340c between them. The body portion 340c defines a bore 340d that is in communication with the bore 330d defined by the shaft portion 330 and the bore 310d defined by the supporting platform portion 310. The support frame also includes mounting means 342, 344, 346 such as mounting screws, pins, rods, bolts, and/or other types of anchoring mechanisms that are configured to securely mount the base portion 340 to the skull 150 of a living subject.

As shown, the adjustable surgical platform 200 has a probe 201a, 201b, 201c guided on a trajectory through a bore (not shown) of a body portion 202 of the adjustable surgical platform 200, and the trajectory continues through the bore 310d defined by the body portion 310c of the support platform portion 310, through the bore 330d of the shaft portion 330, and through the bore 340d of the base portion 340 to a target area of a living subject located inside the skull 150 of a living subject. For example, the probe 201a, 201b may provide an electrical stimulation lead with an electrode for deep brain stimulation (DBS). The leg members 210, 212, 214 connect to the body portion 202 of the adjustable surgical platform 200 at connections 211, 213, 215 and have respective ball portions 216, 218, 220 for engaging with the engaging means 318, 320, 322 disposed on arm portions 312, 314, 318 of the support platform portion 310.

As shown, each of the arm portions 312, 314, 316 is configured to elevate a respective one of the engaging means 318, 320, 322 from the body portion 310c of the supporting platform portion 310 in a second direction that is substantially opposite the first direction. More particularly, as shown the arm portions 312, 314, 316 have a generally upward-curving side profile to provide for an elevated engagement position for the engaging means 318, 320, 322 with corresponding ball portions 214, 216, 218 of the surgical platform 200. It should be appreciated that other configurations may be used for achieving the elevated position of the engagement means other than those shown in the exemplary embodiment of FIGS. 3A and 3B, without departing from the scope of the present invention according to aspects disclosed herein. For example, one or more of the arm portions 312, 314, 316 may have a planar side profile such that the arm portions 312, 314, 316 extend from the body portion 310c of the support platform portion 310, in a direction such that an angle is established between the arm portions 312, 314, and 316 between the planar axis of the body portion 310c and the planar axis of the arm portions 312, 314, 316. Further, it should be appreciated that one or more of the arm portions 312, 314, 316 may be configured to adjustably vary the height at which the engaging means 318, 320, 322 are elevated in relation to the body portion 310c, without departing from the scope of the present invention according to aspects disclosed herein.

Figure 4A:
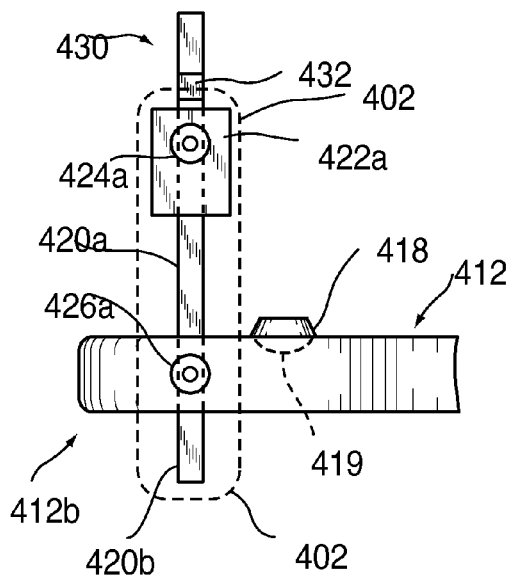
FIG. 4A schematically shows a side view of a means for securing a surgical tracking instrument to a support frame, according to one exemplary embodiment of the present invention.
Figure 4B:
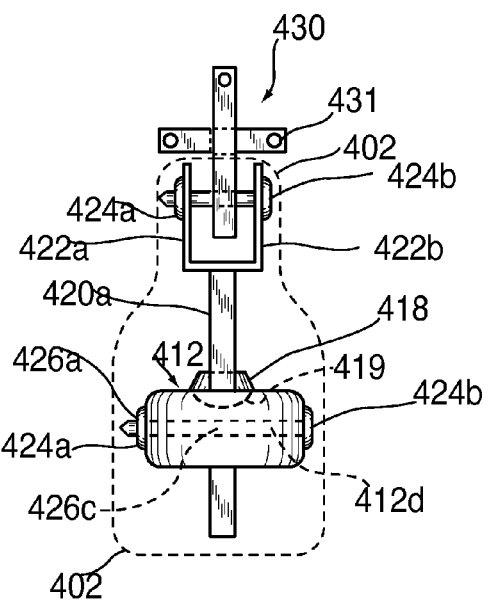
FIG. 4B schematically shows a view of the means for securing a surgical tracking instrument to the support frame shown in FIG. 4A.
Figure 5:
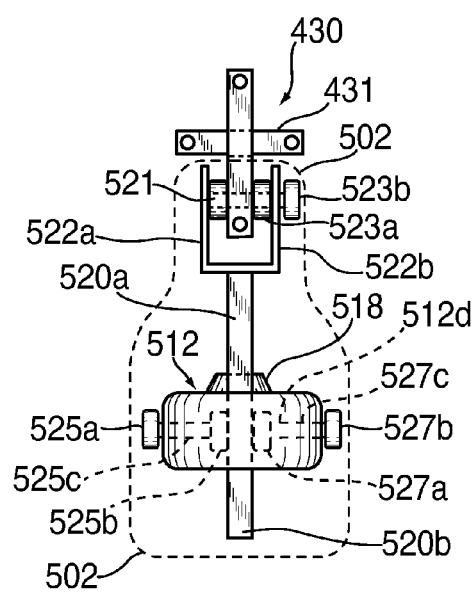
FIG. 5 schematically shows a front view of a means for securing a surgical tracking instrument to a support frame, according to one embodiment of the present invention.

Now referring to FIGS. 4A and 4B, FIG. 4A schematically shows a side, cross-sectional view of a means 402 for securing a surgical tracking instrument 430 to a support frame 100, according to one exemplary embodiment of the present invention, and FIG. 4B schematically shows a front, cross-sectional view of the means 402 shown in FIG. 4A. As shown, the means 402 is positioned proximate to the second end 412b of an arm portion 412 such as an arm portion 112 shown in the embodiment of FIGS. 1A, 1B, and 1C, and the means 402 is further positioned proximate to the engaging means 418, which has a concave recess portion 419. It should be appreciated that the means 402 may be mounted to more than one of the arm portions of a support platform portion, such as the other arm portions 114, 116 of the support platform portion 110 shown in FIGS. 1A, 1B, and 1C, without departing from the scope of the present invention according to aspects disclosed herein.

As shown, the surgical tracking instrument 430 is an optical tracking device with optical emitters 431 and/or detectors for tracking the position of the skull 150 of the living subject with a power and/or data cable 432. It should be appreciated that the surgical tracking instrument 430 is not limited to an optical tracking means and may include one or more other types of surgical instruments for preoperative, intraoperative, or postoperative use, for example fiducial marking devices or other data-acquisition, registration, and/or alignment devices, without departing from the scope of the present invention according to aspects disclosed herein.

Means 402 collectively refers to elements that include an adjustable supporting shaft 420a, 420b, a first side portion 422a, second side portion 422b, and a space for receiving at least a portion of a surgical tracking instrument 430 between them as described above. The surgical tracking instrument 430 is securely engaged by fastening means 422a, 422b, shown as a mounting screw with a locking nut 424a secured at the first side portion 424a and a locking knob 424b at the second side portion 424b, and with a shaft defined between the locking nut 424a and knob portion 424b. The adjustable supporting shaft 420a, 420b is disposed within a vertical bore defined within the body portion 412c such that the adjustable supporting shaft 420a, 420b is adjustably positionable at a desired elevation above the respective arm portion 412, for providing control of the position of the surgical tracking instrument 430 in relation to other elements of a support platform portion and/or adjustable surgical platform as shown in embodiments of FIG. 1A, 1B, 1C, 2A, and 2B. The supporting shaft 420a, 420b is adjustably secured to the arm portion 412 by a fastening means 426a, 426b, which is shown as a locking mounting screw with a locking nut 426a, an opposite, locking knob 424b, and a shaft defined between the locking nut 426a and locking knob 426b. The shaft of the fastening means 426a, 426b extends through a bore 412d in the body portion 412c of the arm portion 412, and through a bore 426c in the supporting shaft 420a, 420b.

Now referring specifically to FIG. 5, a front, cross-sectional view of a means 502 for securing a surgical tracking instrument 430 to a support frame 100 is shown, according to one embodiment of the present invention. The means 502 is positioned proximate to the second end of an arm portion 512, for example arm portion 112 as shown in the embodiment of FIGS. 1A, 1B, and 1C. Further, as shown, the means 502 is further positioned proximate to the engaging means 519. It should be appreciated that means 502 may be mounted to more than one of the arm portions of a support platform portion, such as one or more of the other arm portions 114, 116 of the support platform portion 110 as shown in FIGS. 1A, 1B, and 1C, without departing from the scope of the present invention according to aspects disclosed herein. As shown, the surgical tracking instrument 430 is an optical tracking device with optical emitters 431 and/or detectors for tracking the position of the skull 150 of the living subject intraoperatively. The surgical tracking instrument is provided with a power and/or data cable 432. It should be appreciated that the surgical tracking instrument 430 is not limited to an optical tracking means and may include one or more other types of surgical instruments for preoperative, intraoperative, or postoperative use, for example fiducial marking devices or other data-acquisition, registration, and/or alignment devices, without departing from the scope of the present invention according to aspects disclosed herein.

Means 502 collectively refers to elements that include an adjustable supporting shaft 520a, 520b, a first side portion 522a, a second side portion 522b, and a space defined between the first side portion 522a and second side portion 522b for receiving at least a portion of the surgical tracking instrument 430. The surgical tracking instrument 430 is securely engaged to the adjustable supporting shaft 520a, 520b by fastening means 521, 523a, 523b, which as shown correspond to a threaded adjustable clamp that is configured to be rotated at a locking knob portion 523, to cause a shaft portion to move in a direction from the second side portion 522b towards the first side portion 522a, to thereby urge an engaging portion 523a, such as a flat planar member, to apply a pressing force to one side of the surgical tracking device 430 in a first direction. A bracing member 521 is positioned on another side of the surgical tracking device 430, such that the pressing force from the engaging portion 523a causes the surgical tracking device 430 to be secured in place between the first end portion 522a and the second end portion 522b.

The adjustable supporting shaft 520a, 520b is configured to be adjustably positioned at a desired elevation above the respective arm portion 512 for controlling the position of the surgical tracking instrument 430 in relation to other elements of a support platform portion and/or adjustable surgical platform as shown in embodiments of FIG. 1A, 1B, 1C, 2A, and 2B. The supporting shaft 520a, 520b is adjustably secured to an arm portion 512 by fastening means 525a, 525b, 525c and 527a, 527b, 525c, which form threaded adjustable clamp portions that are configured to be rotated at respective locking knobs 525a, 527b in order to urge shaft portions 525c, 527c through a bore in the respective arm portion 512 to thereby cause flat planar members 525b, 527a at opposite respective ends to apply pressing force against respective sides of the surgical tracking device 430 to secure the surgical tracking device in a fixed position.

It should be noted that the adjustable supporting shaft 520a, 520b in the embodiment shown in FIG. 5 is adjustable in 360° in relation to the directional orientation of the arm portion 512, by rotating the adjustable supporting shaft, which is formed substantially in a cylindrical shape or with another geometry allowing for rotation within the arm portion 512. As discussed above, the adjustable supporting shaft 520a, 520b is also adjustable vertically, to position an attachable surgical tracking device 430 at a desired height above the arm portion 512.

Figure 6A:
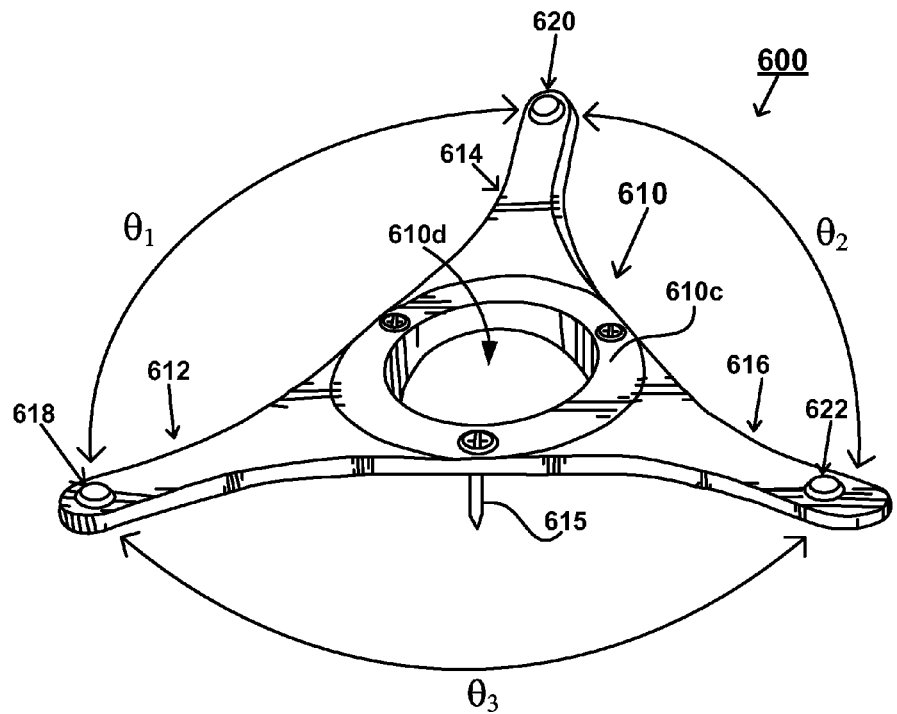
FIG. 6A schematically shows a perspective view of a support frame according to one exemplary embodiment of the present invention.
Figure 6B:
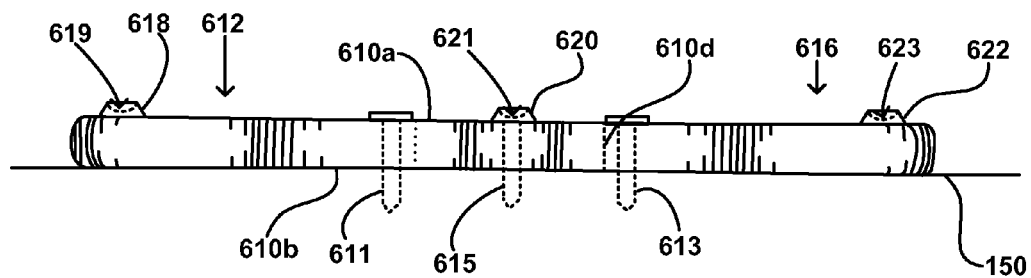
FIG. 6B schematically shows a side view of the support frame shown in FIG. 6A.

Now referring specifically to FIGS. 6A and 6B, a support frame 600 is shown, according to one exemplary embodiment of the present invention. Particularly, FIG. 6A provides a perspective view of the support frame 600 and FIG. 1B provides a side view of the support frame 600. As shown, the support frame 600 includes a supporting platform portion 610 with a substantially annular body portion 610c that defines a bore 610d between a first end portion 610a and a second, opposite end portion 610b, along a central axis. A plurality of arm portions 612, 614, 616 extend radially from the supporting platform portion 610 around the central axis, and are separated from each other by angles $\theta_1, \theta_2, \theta_3$, which are each about 120°. Each of the arm portions 612, 614, 616 has a first end portion 612a, 614a, 616a connected to the body portion 610c of the supporting platform portion 110, a second, opposite end portion 612b, 614b, 616b, and a body portion 612c, 614c, 616c defined between the first end portion 612a, 614a, 616a, and the second end portion 612b, 614b, 616b, respectively. A plurality of engaging means 618, 620, 622 are each positioned on a respective one of the arm portions 612, 614, 616, proximate to the respective second end portions 612b, 614b, 616b of the arm portions 612, 614, 616. Fastening means 611, 613, 615 such as mounting screws, bolts, or pins are provided through the body portion 610c of the supporting platform portion 610, to securely attach the supporting platform portion 610 to a region of interest 150, such as the skull, of a living subject.

Now referring also to the exemplary embodiment shown in FIGS. 7A and 7B, each of the engaging means 618, 620, 622 is configured to engage a leg member 210, 212, 214 of an adjustable surgical platform 200. In this embodiment, the engaging means 618, 620, 622 of each of the arm portions 612, 614, 616 is adjustable in three-dimensions to provide an adjustable positioning angle for corresponding engaged leg members 210, 212, 214 of the adjustable surgical platform 200. Each of the engaging means 618, 620, 622 has a socket-ball joint with a respective concave recess 619, 621, 623 configured to receive a respective ball portion 216, 218, and 220 of a respective one of a plurality of leg members 210, 212, and 214 of the adjustable surgical platform 200. It should be appreciated that other engaging means may be used without departing from the scope of the present invention according to aspects disclosed herein. For example, other types of mechanical joints or interfaces may be used to provide for rotational or other movement for adjustment of a surgical platform in connection with one or more leg members of the adjustable surgical platform.

Now referring specifically to the exemplary embodiments of FIGS. 7A and 7B, FIG. 7A schematically shows a perspective view of a support frame 600 according to the exemplary embodiment shown in FIGS. 6A and 6B, supporting an adjustable surgical platform 200, and FIG. 7B schematically shows a side view of the support frame 600 according to the exemplary embodiment shown in FIGS. 6A and 6B, supporting the adjustable surgical platform 200. The adjustable surgical platform 200 has a probe 201a, 201b, 201c guided on a trajectory through a bore (not shown) of a body portion 202 of the adjustable surgical platform 200, and the trajectory continues through the bore 610d defined by the body portion 610c of the supporting platform portion 610 to a target area located inside the skull 150 of a living subject. For example, the probe 201a, 201b may provide an electrical stimulation lead for deep brain stimulation (DBS) or include a biopsy needle. The leg members 210, 212, 214 connect to the body portion 202 of the adjustable surgical platform 200 at connections 211, 213, 215 and have respective ball portions 216, 218, 220 for engaging with the engaging means 618, 620, 622 disposed on arm portions 612, 614, 618 of the supporting platform portion 610.

Figure 8A:
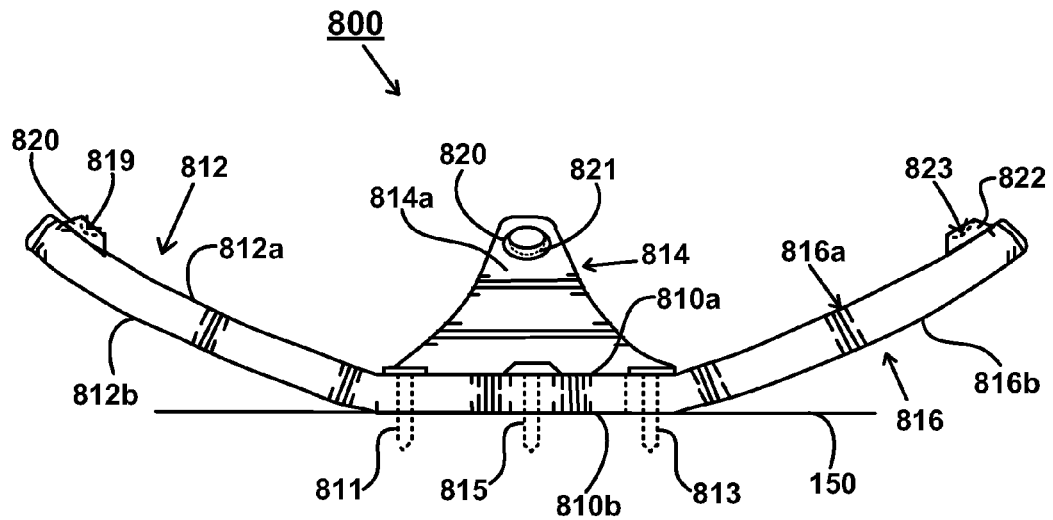
FIG. 8A schematically shows a side view of a support frame according to one exemplary embodiment of the present invention.
Figure 8B:
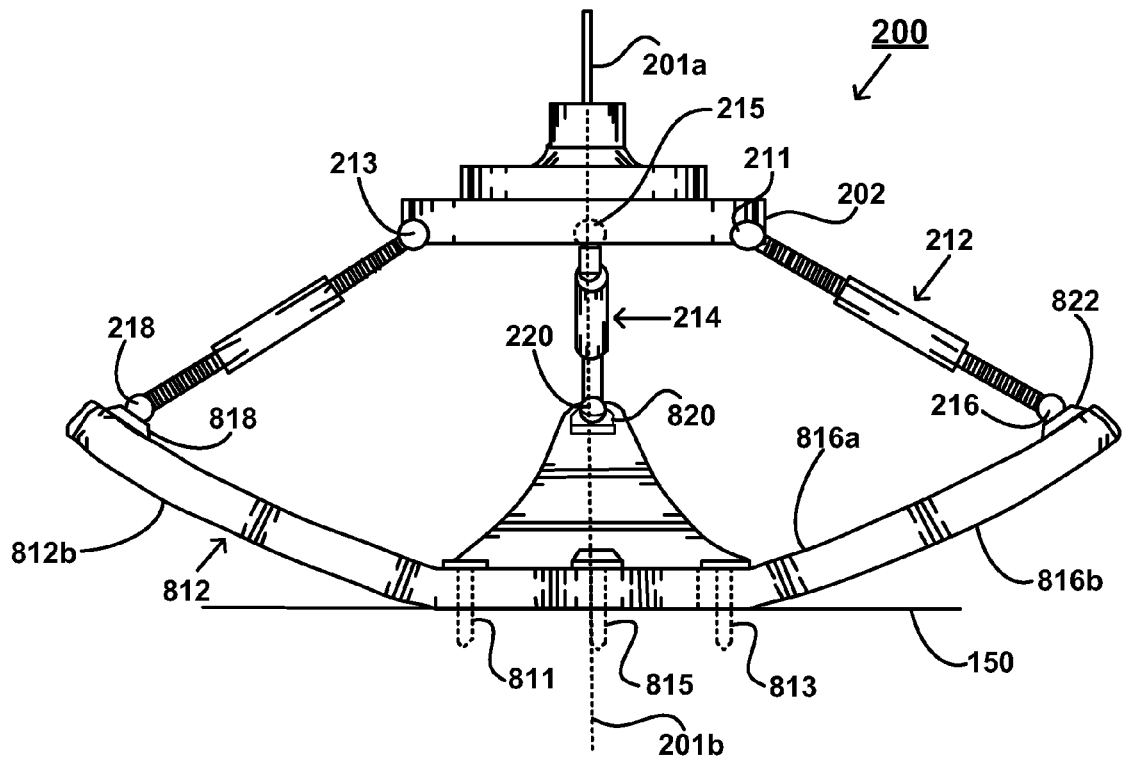
FIG. 8B schematically shows a side view of the support frame shown in FIG. 8A, supporting an adjustable surgical platform.

Now referring specifically to FIGS. 8A and 8B, FIG. 8A schematically shows a side view of a support frame 800 according to one exemplary embodiment of the present invention, and FIG. 8B schematically shows a side view of the support frame 800 shown in FIG. 8A, supporting an adjustable surgical platform 200. As shown, the support frame 800 includes a supporting platform portion 810 with a substantially annular body portion 810c that defines a bore 810d between a first end portion 810a and a second, opposite end portion 810b, along a central axis. A plurality of arm portions 812, 814, 816 extend radially from the supporting platform portion 810 around the central axis, separated from each other by angles $\theta_1$, $\theta_2$, $\theta_3$, which are each about 120°. Each of the arm portions 812, 814, 816 has a respective first end portion 812a, 814a, 816a connected to the body portion 810c of the supporting platform portion 810, a second, opposite end portion 812b, 814b, 816b, and a body portion 812c, 814c, 816c defined between the first end portion 812a, 814a, 816a and the second end portion 812b, 814b, 816b, respectively. A plurality of engaging means 818, 820, 322 are each positioned on respective one of the arm portions 812, 814, 816, proximate to the respective second end portions 812b, 814b, 816b of the arm portions 812, 814, 816. Fastening means 811, 813, 815 such as mounting screws, bolts, or pins are provided through the body portion 810c of the supporting platform portion 810, to securely attach the supporting platform portion 810 to the skull 150 of a living subject.

As shown, the adjustable surgical platform 200 has a probe 201a, 201b, 201c guided on a trajectory through a bore (not shown) of a body portion 202 of the adjustable surgical platform 200, and the trajectory continues through the bore 810d defined by the body portion 810c of the support platform portion 810 to a target area located inside the skull 150 of a living subject. For example, the probe 201a, 201b may provide an electrical stimulation lead for deep brain stimulation (DBS) or include a biopsy needle. The leg members 210, 212, 214 connect to the body portion 202 of the adjustable surgical platform 200 at connections 211, 213, 215 and have respective ball portions 216, 218, 220 for engaging with the engaging means 818, 820, 822 disposed on arm portions 812, 814, 818 of the support platform portion 810.

As shown, each of the arm portions 812, 814, 816 is configured to elevate a respective one of the engaging means 818, 820, 822 from the body portion 810c of the supporting platform portion 810. More particularly, as shown the arm portions 812, 814, 816 have a generally upward-curving side profile to provide for an elevated engagement position for the engaging means 818, 820, 822 with corresponding ball portions 214, 216, 218 of the surgical platform 200. It should be appreciated that other configurations may be used for achieving the elevated position of the engagement means other than those shown in the exemplary embodiment of FIGS. 8A and 8B, without departing from the scope of the present invention according to aspects disclosed herein. For example, one or more of the arm portions 812, 814, 816 may have a planar side profile such that the arm portions 812, 814, 816 extend from the body portion 810c of the support platform portion 810, in a direction such that an angle is established between the arm portions 812, 814, and 816 between the planar axis of the body portion 810c and the planar axis of the arm portions 812, 814, 816. Further, it should be appreciated that one or more of the arm portions 812, 814, 816 may be configured to adjustably vary the height at which the engaging means 818, 820, 822 are elevated in relation to the body portion 810c, without departing from the scope of the present invention according to aspects disclosed herein.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:
1. A surgical apparatus comprising:
an adjustable surgical platform, comprising:
a ring structure having a first end portion, and an opposite, second end portion, and a body portion therebetween, wherein the body portion defines a housing extending between the first and second end portions;
a ball joint having a center and received in the housing of the ring structure and rotatable around its center, wherein the ball joint defines at least one bore for accommodating a probe therethrough; and
a plurality of leg members having a joint portion connected to the ring structure, an exteriorly threaded shank portion extending away from the joint portion, and an axis through the joint portion and the exteriorly threaded shank portion;
a support apparatus comprising:
a supporting platform portion having a body portion defining a bore along a central axis A;
a plurality of arm portions, each extending radially from the supporting platform portion around the central axis A;
a plurality of engaging portions, each positioned on a respective one of the arm portions and configured to detachably engage and secure one of the leg members of the surgical platform such that the surgical platform can be securely mounted to the support apparatus;
a shaft portion extending from the supporting platform portion in a first direction, having a shaft body portion defining a bore along a longitudinal axis B that is in communication with the bore of the supporting platform portion;
a base portion connected to the shaft portion and defining a bore in communication with the bore of the shaft portion and the bore of the supporting platform portion; and
a mounting portion configured to secure the base portion to a region of interest of a living subject.

2. The surgical apparatus of claim 1, wherein at least one of the engaging portions is disposed proximate a second end of a respective at least one of the plurality of arm portions.

3. The surgical apparatus of claim 1, wherein at least one of the arm portions is configured to elevate a respective one of the engaging portions from the supporting platform portion in a second direction that is substantially opposite the first direction.

4. The surgical apparatus of claim 1 wherein the at least one of the engaging portions is adjustable in three-dimensions to provide an adjustable positioning angle for an engaged leg member of the adjustable surgical platform.

5. The surgical apparatus of claim 1, wherein the plurality of arm portions are separated at angles $\theta_1$, $\theta_2$, $\theta_3$ from each other around the central axis A and the angles $\theta_1$, $\theta_2$, $\theta_3$ are the same or different.

6. The surgical apparatus of claim 1, wherein the mounting portion comprises at least one fastening means configured to secure the base portion to the region of interest of the living subject.

7. The surgical apparatus of claim 1, further comprising a means for securing a surgical tracking instrument to one of the plurality of arm portions.

8. A surgical apparatus comprising:
an adjustable surgical platform, comprising:
a ring structure having a first end portion, and an opposite, second end portion, and a body portion therebetween, wherein the body portion defines a housing extending between the first and second end portions;
a ball joint having a center and received in the housing of the ring structure and rotatable around its center, wherein the ball joint defines at least one bore for accommodating a probe therethrough; and
a plurality of leg members having a joint portion connected to the ring structure, an exteriorly threaded shank portion extending away from the joint portion, and an axis through the joint portion and the exteriorly threaded shank portion;
a support apparatus, comprising:
a supporting platform portion having a body portion defining a bore between a first end portion and a second, opposite end portion along a central axis A;
a plurality of arm portions, each extending radially from the supporting platform portion around the central axis A, each arm portion having a first end portion connected to the body portion of the supporting platform portion, a second, opposite end portion, and a body portion defined therebetween;
a plurality of engaging portions, each positioned on a respective one of the plurality of arm portions proximate the respective second end portions and configured to detachably engage and secure one of the leg members of the surgical platform such that the surgical platform can be securely mounted to the support apparatus;
a shaft portion extending from the second end portion of the supporting platform portion in a first direction, having a first end portion connected to the body portion of the supporting platform portion, an opposite, second end portion, and a shaft body portion defined between the first end portion and the second end portion and defining a bore along a longitudinal axis B that is in communication with the bore defined by the supporting platform portion, wherein the longitudinal axis B is substantially parallel to the central axis A;
a base portion connected to the second end portion of the shaft portion, having a first end portion and an opposite, second end portion defining a body portion therebetween, the body portion defining a bore that is in communication with the bore defined by the shaft portion and the bore defined by the supporting platform portion; and
a mounting portion configured to mount the base portion to the skull of a living subject.

9. The surgical apparatus of claim 8, wherein each of the arm portions is configured to elevate a respective one of the engaging portions from the body portion of the supporting platform portion in a second direction that is substantially opposite the first direction.

10. The surgical apparatus of claim 8, wherein the engaging portions of each of the arm portions are adjustable in three-dimensions to provide an adjustable positioning angle for corresponding engaged leg members of the adjustable surgical platform.

11. The surgical apparatus of claim 10, wherein each leg member comprises a ball portion and wherein each of the plurality of engaging portions is configured to engage the ball portion of a respective leg member of the adjustable surgical platform.

12. The surgical apparatus of claim 11, wherein each of the plurality of engaging portions comprises a socket portion of a socket-ball joint.

13. The surgical apparatus of claim 11, wherein each of the engaging portions comprises a concave recess.

14. The surgical apparatus of claim 8, wherein the plurality of arm portions are separated at equal angles $\theta_1$, $\theta_2$, $\theta_3$ from each other around the central axis A.

15. The surgical apparatus of claim 14, wherein the plurality of arm portions comprises three arm portions separated 120° from each other around the central axis A.

16. The surgical apparatus of claim 8, wherein the mounting portion comprises at least one fastening portion configured to secure the base portion to the skull of the living subject.

17. The surgical apparatus of claim 8, further comprising a means for securing a surgical tracking instrument to one of the plurality of arm portions.

18. A surgical apparatus comprising:
an adjustable surgical platform, comprising:
a ring structure having a first end portion, and an opposite, second end portion, and a body portion therebetween, wherein the body portion defines a housing extending between the first and second end portions;
a ball joint configured to be received in the housing of the ring structure and be rotatable around its center, wherein the ball joint defines at least one bore for accommodating a probe therethrough; and
a plurality of leg members having a joint portion connected to the ring structure, an exteriorly threaded shank portion extending away from the joint portion, and an axis through the joint portion and the exteriorly threaded shank portion;
a support apparatus, comprising:
a supporting platform portion having an annular body portion defining a bore between a first end portion and second, opposite end portion along a central axis A;
a plurality of arm portions extending radially from the annular body portion around the central axis A, each arm portion having a first end portion connected to the annular body portion, a second, opposite end portion, and a body portion defined therebetween;

a plurality of engaging portions, each positioned on a respective one of the arm portions proximate the second end portion and configured to detachably engage and secure one of the leg members of the surgical platform such that the surgical platform can be securely mounted to the support apparatus;

a shaft portion extending from the second end portion of the annular body portion in a first direction, having a first end portion connected to the annular body portion, an opposite, second end portion, and a body portion defined therebetween and defining a bore along a longitudinal axis B that is in communication with the bore defined by the supporting platform portion, wherein the longitudinal axis B is substantially parallel to the central axis A;

a base portion connected to the second end of the shaft portion, having a first end portion and an opposite, second end portion defining body portion therebetween, the body portion defining a bore that is in communication with the bore defined by the shaft portion and the bore defined by the supporting platform portion; and a mounting portion configured to mount the base portion to the skull of a living subject.

19. The surgical apparatus of claim 18, wherein each of the arm portions is configured to elevate a respective one of the engaging portions from the body portion of the supporting platform portion in a second direction that is substantially opposite the first direction.

20. The surgical apparatus of claim 18, wherein each of the engaging portions is adjustable in three-dimensions to provide an adjustable positioning angle for a corresponding engaged leg member of the adjustable surgical platform.

21. The surgical apparatus of claim 18, wherein the plurality of arm portions comprises three arm portions separated 120° from each other around the central axis A.

22. The surgical apparatus of claim 18, wherein the mounting portion comprises at least one fastening means configured to secure the base portion to the skull of the living subject.

23. The surgical apparatus of claim 18, further comprising a means for securing a surgical tracking instrument to one of the plurality of arm portions.

* * * * *